United States Patent
Lee et al.

(10) Patent No.: US 12,377,111 B2
(45) Date of Patent: Aug. 5, 2025

(54) COMPOSITION, COMPRISING THIAMINE DERIVATIVE, FOR PREVENTION OR TREATMENT OF HYPERCORTISOLEMIA

(71) Applicant: KYUNGPOOK NATIONAL UNIVERSITY INDUSTRY-ACADEMIC COOPERATION FOUNDATION, Daegu (KR)

(72) Inventors: In Kyu Lee, Daegu (KR); Jae Han Jeon, Daegu (KR); Hyeon-Ji Kang, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 982 days.

(21) Appl. No.: 17/274,274

(22) PCT Filed: Sep. 30, 2019

(86) PCT No.: PCT/KR2019/012723
§ 371 (c)(1),
(2) Date: Mar. 8, 2021

(87) PCT Pub. No.: WO2020/067832
PCT Pub. Date: Apr. 2, 2020

(65) Prior Publication Data
US 2021/0308156 A1    Oct. 7, 2021

(30) Foreign Application Priority Data
Sep. 28, 2018   (KR) .................. 10-2018-0116372

(51) Int. Cl.
*A61P 37/04*   (2006.01)
*A61K 31/505*   (2006.01)
(Continued)

(52) U.S. Cl.
CPC .......... *A61K 31/675* (2013.01); *A61K 31/505* (2013.01); *A61K 31/51* (2013.01); *A61P 37/04* (2018.01)

(58) Field of Classification Search
CPC .... A61K 31/675; A61K 31/505; A61K 31/51; A61P 37/04
See application file for complete search history.

(56) References Cited

U.S. PATENT DOCUMENTS 9,718,846 B1   8/2017 Zhong et al.
2003/0077254 A1   4/2003 Ramaekers

FOREIGN PATENT DOCUMENTS

DE   102007053804 A1   5/2009
JP   2017-036271 A   2/2017
(Continued)

OTHER PUBLICATIONS

Markova, N.; Bazhenova, N.; Anthony, D. C.; et al. "Thiamine and benfotiamine improve cognition and ameliorate GSK-3β-associated stress-induced behaviors in mice" Progress in Neuro-Psychopharmacology & Biological Psychiatry 75 (2017) 148-156. (Year: 2017).*

(Continued)

*Primary Examiner* — Andrew D Kosar
*Assistant Examiner* — John D McAnany
(74) *Attorney, Agent, or Firm* — Clark & Elbing LLP (57) ABSTRACT

The present invention relates to a composition for prevention or treatment of hypercortisolemia, the composition comprising allithiamine, fursultiamine, and benfotiamine, which are all derivatives of thiamine, or a mixed composi-
(Continued)

tion thereof. The composition for prevention or treatment of hypercortisolemia of the present invention can effectively treat or alleviate symptoms or disorders resulting from excessive secretion of cortisol, without surgical operations, and does not exhibit side effects caused by conventional medications.

3 Claims, 7 Drawing Sheets

(51) Int. Cl.
*A61K 31/51* (2006.01)
*A61K 31/675* (2006.01)

(56) References Cited

FOREIGN PATENT DOCUMENTS

| KR | 10-2002-0069171 A | 8/2002 |
| KR | 10-2014-0030327 A | 3/2014 |
| KR | 10-2014-0144418 A | 12/2014 |
| KR | 10-1487231 B1 | 1/2015 |

OTHER PUBLICATIONS

Joels, M.; Karst, H.; Sarabdjitsingh, R. A. "The stressed brain of humans and rodents" Acta Physiologica. Apr. 2018;223:e13066. (Year: 2018).*
Feelders, R. A.; Hofland, L. J. "Medical Treatment of Cushing's Disease" J Clin Endocrinol Metab, Feb. 2013, 98(2):425-438. (Year: 2013).*
Park, W.; Lee, J.; Hong, T.; et al. "Comparative Pharmacokinetic Analysis of Thiamine and Its Phosphorylated Metabolites Administered as Multivitamin Preparations" Clinical Therapeutics/vol. 38, No. 10, 2016. (Year: 2016).*
Gulati et al., Chapter 16: Nutraceuticals as Adaptogens: Their Role in Health and Disease, Neutraceuticals 193-205 (2016).
International Search Report mailed Jan. 22, 2020, for PCT International Application PCT/KR2019/012723, Lee et al., "Composition, Comprising Thiamine Derivative, for Prevention or Treatment of Hypercortisolemia," filed Sep. 30, 2019 (9 pages).
Extended European Search Report dated Oct. 20, 2021 for European Patent Application No. 19864600.2 (8 pages).

* cited by examiner

COMPOSITION, COMPRISING THIAMINE DERIVATIVE, FOR PREVENTION OR TREATMENT OF HYPERCORTISOLEMIA

TECHNICAL FIELD

The present disclosure is made with the support of the Ministry of Science and ICT, Republic of Korea, under Project No. NRF-2017R1A2B3006406, which was conducted in the research project named "New Therapeutic Mechanism of Chronic Inflammation and Metabolic Syndrome through Mitochondria-Associated ER Membrane (MAM) Interaction and Pyruvate Dehydrogenase Kinase (PDK) Activity Regulation" in the research program titled "Mid-Career Research", by the Kyungpook National University Industry-Academic Cooperation Foundation, under the research management of the National Research Foundation of Korea, from 1 Mar. 2017 to 28 Feb. 2022.

The present disclosure was also made with the support of the Ministry of Health and Welfare, Republic of Korea, under Project No. HI16C1501, which was conducted in the research project named "Leading-edge Research Center for Drug Discovery and Development for Diabetes and Metabolic Disease" in the research program titled "Leading Characterization Research Program", by the Kyungpook National University Hospital, under the research management of the Korea Health Industry Development Institute, from 1 Apr. 2016 to 31 Mar. 2021.

This application claims priority to and the benefit of Korean Patent Application No. 10-2018-0116372 filed in the Korean Intellectual Property Office on 28 Sep. 2018, the disclosure of which is incorporated herein by reference.

The present disclosure relates to a composition containing a thiamine derivative for prevention or treatment of hypercortisolism and, more specifically, to a composition for prevention or treatment of hypercortisolism, the composition containing a thiamine derivative, a salt thereof, or a mixture composition thereof, the thiamine derivative being allithiamine, fursultiamine, or benfotiamine.

BACKGROUND ART

Adrenocorticotropin (ACTH) is a hormone that is essential for normal steroidogenesis and the maintenance of adrenal weight. ACTH is secreted by the pituitary gland in response to physiological or psychological stress, and mainly increases the production and release of corticosteroids. In particular, ACTH is secreted from corticotropes in the adenohypophysis of the pituitary gland in response to the release of the corticotropin-releasing hormone (CRH) by the hypothalamus. Once secreted, ACTH travels to the adrenal cortex, and binds to and activates melanocortin 2 receptors (MC2R). Activation of MC2R results in the production of cAMP in the adrenal cell, and cAMP binds to protein kinase (PKA), which activates the conversion of the lipid cholesterol to the steroid hormone cortisol.

Cortisol affects numerous biological processes in order to restore homeostasis after stress. For example, cortisol regulates glucose homeostasis, increases blood pressure, promotes gluconeogenesis, promotes metabolism of glycogen, lipids, and proteins, and suppresses immune responses. Under normal physiological conditions, cortisol levels are tightly regulated, but in some diseases and disorders, cortisol levels are elevated. The overproduction of cortisol damages the hippocampus, a region of the brain that is critical for regulation of the hypothalamus/pituitary/adrenal axis. In addition, symptoms, such as increased fat accumulation, increased blood pressure levels, increased blood sugar levels, bone loss, muscle weakness, and lowered immunity, are shown.

In order to normalize the hypersecretion of cortisol, adrenalectomy, which is a surgical operation, is mainly performed. However, adrenalectomy results in the removal of both adrenal glands, and thus continuous steroid hormone supplementation is required after surgery. Meanwhile, patients who cannot undergo surgery can receive radiation therapy for the pituitary gland, but it takes a long time to exhibit sufficient therapeutic effects, and pituitary dysfunction is likely to develop. Enzyme inhibitors to inhibit cortisol synthesis, such as metyrapone, aminoglutethimide, and ketoconazole, may be used, but these medications are mainly used as adjuvant therapy due to undefined medicinal effects and many side effects thereof. The finding of therapeutic substances for effectively treating, without surgical operation, symptoms or diseases caused by over-release of cortisol is required.

Allithiamine, fursultiamine, and benfotiamine, which are vitamin B1 (thiamine) derivatives, are fat-soluble and active vitamins with high bioavailability. Allithiamine is an asymmetric disulfide-type thiamine derivative produced by the reaction of vitamin B1 and allicin generated from garlic alliin. Allithiamine has advantages of showing excellent intestinal absorption owing to its fat-soluble properties and not being degraded by thiaminase. Fursultiamine is obtained from the modification of residues of a disulfide linkage (-s-s-) portion of the allithiamine, and has been known to be an active vitamin that plays an important role in neurons and muscles. Benfotiamine, which is an S-acyl derivative of thiamine, enhances immunity and protects brain functions, and mainly acts on peripheral tissues by increasing trans-ketolase activity.

The present inventors have found that allithiamine, fursultiamine, and benfotiamine proven to have in vivo stability effectively inhibit the secretion of cortisol, and then the present inventors intended to propose these substances as therapeutic agents for inhibiting hypercortisolism or cortisol overproduction.

DETAILED DESCRIPTION OF THE INVENTION

Technical Problem

The present inventors have undertaken intensive research efforts to develop novel therapeutic agents capable of inhibiting overproduction of the steroid hormone cortisol. As a result, the present inventors have found that allithiamine, fursultiamine, and benfotiamine among thiamine derivatives have a cortisol production inhibitory effect.

Therefore, an aspect of the present disclosure is to provide a pharmaceutical composition for prevention or treatment of hypercortisolism.

Another aspect of the present disclosure is to provide a food composition for alleviation of hypercortisolism.

Still another aspect of the present disclosure is to provide a pharmaceutical composition for prevention or treatment of cortisol-induced hypertension, diabetes, obesity, depression, or acute stress.

Still another aspect of the present disclosure is to provide a food composition for alleviation of cortisol-induced hypertension, diabetes, obesity, depression, or acute stress.

Still another aspect of the present disclosure is to provide a method for regulating or inhibiting cortisol secretion by administering to a subject a pharmaceutical composition containing at least one compound selected from the group consisting of allithiamine, fursultiamine, benfotiamine, and pharmaceutically acceptable salts thereof.

Technical Solution

In accordance with an aspect of the present disclosure, there is provided a pharmaceutical composition for prevention or treatment of hypercortisolism, the pharmaceutical composition containing at least one compound selected from the group consisting of thiamine derivatives and pharmaceutically acceptable salts thereof, the thiamine derivatives being allithiamine, fursultiamine, and benfotiamine.

Chemical formulas 1 to 3 below represent structures of allithiamine, fursultiamine, and benfotiamine, respectively.

[Chemical Formula 1]

[Chemical Formula 2]

[Chemical Formula 3]

The present inventors have undertaken intensive research efforts to develop novel therapeutic agents capable of inhibiting excessive secretion of the steroid hormone cortisol, and as a result, the present inventors have found that allithiamine, fursultiamine, and benfotiamine among thiamine derivatives have a cortisol production inhibitory effect, and thus completed the present disclosure.

As used herein, the term "hypercortisolism" is used to encompass all symptoms or diseases in which in vivo cortisol production increases, and may be used in the same meaning as cortisol hypersecretion or hypercortisolemia. For instance, hypercortisolism may refer to a case where blood cortisol levels are measured in excess out of the normal range. The causes of cortisol hypersecretion are, but are not limited to, long-term exposure to cortisol through drugs or the like, tumors that overproduce cortisol, tumors that are caused by overproduced cortisol, and the like.

According to an embodiment, example of symptoms or diseases causing overproduction of cortisol include, but are not limited to, Cushing's syndrome, Cushing's disease, ectopic adrenocorticotropic hormone syndrome, or the like.

As used herein, the term "Cushing's syndrome" refers to a general state in which the level of cortisol, a type of glucocorticoid, is high in the blood. This syndrome have symptoms, such as moon face, buffalo hump (hump at the posterior part of cervical vertebrae), truncal obesity, facial plethora, acne, hirsutism, amenorrhea, decreased sexual function, osteoporosis, hypertension, depression, and the like.

As used herein, the term "Cushing's disease" refers to an excess state of cortisol in the blood caused by pituitary adenoma (ACTH-secreting adenoma), as a type of Cushing's syndrome.

Most of Cushing's disease patients have accompanied by pituitary microadenoma. Elevated cortisol levels may occur for reasons other than a pituitary tumor, and for example, cortisol levels may be elevated by: tumors of the adrenal glands producing cortisol; and ectopic ACTH production (i.e., certain types of cancer in the body can make ACTH, which then stimulates normal adrenal glands to make excessive cortisol).

Cushing's syndrome resulting from ectopic ACTH expression is frequently caused by neoplasms including small cell lung cancer, non-small cell lung cancer (NSCLC), pancreatic carcinoma, neural tumors (such as gliomas, neuroepitheliomatous neoplasms, or nerve sheath tumors) and thymoma. Small cell lung cancer has been observed to account for up to 50% of Cushing's syndrome of ectopic or neoplastic origin.

Cushing's disease includes recurrent Cushing's disease, refractory Cushing's disease, persistent Cushing's disease, endogenous Cushing's disease, spontaneous hypercortisolism, adrenocorticotropic hormone dependent Cushing's disease, adrenocorticotropic hormone independent Cushing's disease, and the like.

Ectopic adrenocorticotropic hormone syndrome is a cortisol hypersecretion symptom resulting in hyperpigmentation, hypokalemic alkalosis, abnormal glucose tolerance, or the like, and is more common in men.

Examples of the cortisol-induced disease caused by overproduced cortisol may include cortisol-induced hypertension, osteoporosis, depression, diabetes, heart failure, or the like. In addition, high cortisol levels may cause obesity, sleep apnea, adrenal hyperplasia (congenital adrenal hyperplasia), anxiety disorders, muscle atrophy, cognitive dysfunction, galactorrhea, and metabolic syndrome.

The pharmaceutical composition of the present disclosure contains a compound composed of a combination of at least one selected from the group consisting of allithiamine, fursultiamine, benfotiamine, and pharmaceutically acceptable salts thereof. All the above compounds are derivatives of vitamin B1 (thiamine) and fat-soluble vitamins. These are active vitamins with high bioavailability, unlike water-soluble vitamins that are easily excreted out of the body.

The pharmaceutical composition of the present disclosure may contain allithiamine, fursultiamine, benfotiamine, or a salt thereof at an amount sufficient to attain efficacy or activity thereof (therapeutically effective amount). The upper limit of the amount of allithiamine, fursultiamine, benfotiamine, or a salt thereof contained in the composition of the present disclosure may be selected within an appropriate range by a person skilled in the art.

The allithiamine, fursultiamine, and/or benfotiamine used as an active ingredient in the present disclosure may be used as itself or in the form of a salt, preferably a pharmaceutically acceptable salt. The salt is preferably an acid addition salt formed by a pharmaceutically acceptable free acid. The free acid may be an inorganic acid and an organic acid. Examples of the organic acid include, but are not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid, and aspartic acid. Examples of the inorganic acid include, but are not limited to, hydrochloric acid, bromic acid, sulfuric acid, and phosphoric acid.

The pharmaceutical composition of the present disclosure may contain a pharmaceutically acceptable carrier. The pharmaceutically acceptable carrier is typically used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oils, and the like. The pharmaceutical composition of the present disclosure may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in Remington's Pharmaceutical Sciences (19th ed., 1995).

The pharmaceutical composition of the present disclosure may be administered orally or parenterally, and examples of parenteral administration may include intravenous injection, subcutaneous injection, intramuscular injection, intraperitoneal injection, and percutaneous administration.

The appropriate dose of the pharmaceutical composition of the present disclosure varies depending on factors, such as formulation method, administration method, patient's age, body weight, and sex, pathological condition, diet, administration time, administration route, excretion rate, and response sensitivity. An ordinarily skilled practitioner can easily determine and prescribe an administration dose that is effective for desired treatment or prevention. According to a preferable embodiment of the present disclosure, the daily dose of the pharmaceutical composition of the present disclosure is 0.001-10000 mg/kg.

The pharmaceutical composition of the present disclosure may be administered in a single dose or multiple doses. Thiamine-based compounds are cofactors of mitochondrial enzymes, and may be administered in multiple doses at regular intervals in order to continuously activate this enzyme.

The pharmaceutical composition of the present disclosure may be formulated using a pharmaceutically acceptable carrier and/or excipient by a method that may be easily performed by a person skilled in the art to which the present disclosure pertains, so that the composition may be prepared in a unit dosage form or in the form of being contained in a multi-dose container. The formulation may be in the form of a solution in an oily or aqueous medium, a suspension, or an emulsion, or in the form of an extract, a powder, granules, a tablet, or a capsule, and may further contain a dispersant or a stabilizer.

In accordance with another aspect of the present disclosure, there is a food composition for alleviation of hypercortisolism, the food composition containing at least one compound selected from the group consisting of thiamine derivatives and salts thereof, the thiamine derivatives being allithiamine, fursultiamine, and benfotiamine.

Since the food composition of the present disclosure uses an active ingredient the same as allithiamine, fursultiamine, benfotiamine, or a salt thereof, which correspond to an active ingredient of the above-described pharmaceutical composition for prevention or treatment of hypercortisolism of the present disclosure, the description of overlapping contents therebetween is omitted to avoid excessive complexity of the specification.

When the composition of the present disclosure is a food composition, the food composition may be prepared in the form of a powder, granules, a tablet, a capsule, or a drink. Examples thereof are various foods, e.g., candies, drinks, chewing gums, teas, vitamin complexes, health supplement foods, and the like.

The food composition of the present disclosure may contain not only allithiamine, fursultiamine, benfotiamine, or a salt thereof, but also ingredients that are typically added in the manufacturing of foods, and contains, for example, proteins, carbohydrates, fats, nutrients, seasoning agents, and flavoring agents. Examples of the carbohydrates are: saccharides, such as monosaccharides (e.g., glucose and fructose), disaccharides (e.g., maltose, sucrose, and oligosaccharides), and polysaccharides (e.g., dextrin and cyclodextrin); and sugar alcohols, such as xylitol, sorbitol, and erythritol. As flavoring agents, natural flavoring agents [thaumatin, stevia extracts (e.g., rebaudioside A, glycyrrhizin, etc.)] and synthetic flavoring agents (saccharin, aspartame, etc.) may be used. For example, when the food composition of the present disclosure is prepared as a drink, the drink may further contain citric acid, liquid fructose, sugar, glucose, acetic acid, malic acid, fruit juice, a eucommia extract, a jujube extract, a licorice extract, in addition to allithiamine, fursultiamine, benfotiamine, or a salt thereof.

In accordance with still another aspect of the present disclosure, there is provided a pharmaceutical composition for prevention or treatment of cortisol-induced hypertension, diabetes, obesity, depression, or acute stress, the pharmaceutical composition containing at least one compound selected from the group consisting of thiamine derivatives and pharmaceutically acceptable salts thereof, the thiamine derivatives being allithiamine, fursultiamine, and benfotiamine.

Since the pharmaceutical composition for prevention or treatment of cortisol-induced hypertension, diabetes, obesity, depression, or acute stress of the present disclosure uses an active ingredient the same as allithiamine, fursultiamine, benfotiamine, or a salt thereof, which correspond to an active ingredient of the above-described pharmaceutical composition for prevention or treatment of hypercortisolism of the present disclosure, the description of overlapping contents therebetween is omitted to avoid excessive complexity of the specification.

As used herein, the term "cortisol-induced" disease refers to a disease that is caused by excessive secretion or overproduction of cortisol. Examples of the cortisol-induced disease caused by overproduced cortisol may include cortisol-induced hypertension, osteoporosis, depression, diabetes, heart failure, or the like. In addition, high cortisol levels may cause obesity, sleep apnea, adrenal hyperplasia (congenital adrenal hyperplasia), anxiety disorders, muscle atrophy, cognitive dysfunction, galactorrhea, and metabolic syndrome.

In accordance with still another aspect of the present disclosure, there is provided a food composition for alleviation of cortisol-induced hypertension, diabetes, obesity, depression, or acute stress, the food composition containing at least one compound selected from the group consisting of thiamine derivatives and salts thereof, the thiamine derivatives being allithiamine, fursultiamine, and benfotiamine.

Since the food composition for alleviation of cortisol-induced hypertension, diabetes, obesity, depression, or acute stress of the present disclosure uses an active ingredient the same as allithiamine, fursultiamine, benfotiamine, or a salt thereof, which correspond to an active ingredient of the above-described food composition for alleviation of hypercortisolism of the present disclosure, the description of overlapping contents therebetween is omitted to avoid excessive complexity of the specification.

In accordance with still another aspect of the present disclosure, there is provided a method for inhibiting cortisol secretion, the method including a step of administering to a subject a pharmaceutical composition containing at least one compound selected from the group consisting of thiamine derivatives and pharmaceutically acceptable salts thereof, the thiamine derivatives being allithiamine, fursultiamine, and benfotiamine.

As used herein, the term "administration" refers to the provision of a predetermined substance for a patient by any appropriate method, and the pharmaceutical composition of the present disclosure may be administered orally or parenterally through all general routes so long as the pharmaceutical composition can arrive at target tissues. In addition, the composition of the present disclosure may be administered using any apparatus that can deliver an active ingredient to target cells or tissues.

As used herein, the "subject" is not particularly limited, but encompasses, for example, human beings, monkeys, cows, horses, sheep, pigs, chickens, turkeys, quails, cats, dogs, mice, rats, rabbits, or guinea pigs, preferably a mammal, and more preferably a human being.

Advantageous Effects

Features and advantages of the present disclosure are summarized as follows.

(A) The present disclosure is directed to a composition for prevention or treatment of hypercortisolism, the composition containing a thiamine derivative, a salt thereof, or a mixture composition thereof, the thiamine derivative being allithiamine, fursultiamine, or benfotiamine.

(B) The composition for prevention or treatment of hypercortisolism of the present disclosure can effectively treat or alleviate, without surgery operation, symptoms or diseases caused by excessive secretion of cortisol, and has no side effects caused by conventional drugs.

BEST MODE FOR CARRYING OUT THE INVENTION

The present disclosure is directed to a pharmaceutical composition for prevention or treatment of hypercortisolism, the pharmaceutical composition containing at least one compound selected from the group consisting of thiamine derivatives and pharmaceutically acceptable salts thereof, the thiamine derivatives being allithiamine, fursultiamine, and benfotiamine.

MODE FOR CARRYING OUT THE INVENTION

Hereinafter, the present disclosure will be described in more detail with reference to examples. These examples are provided only for the purpose of illustrating the present disclosure in more detail, and therefore, according to the purpose of the present disclosure, it would be apparent to a person skilled in the art that these examples are not construed to limit the scope of the present disclosure.

Example 1: Verification of Cortisol Reduction Effects by Thiamine Derivatives In Vitro Cortisol secretion inhibitory effects by allithiamine (Shanghai iChemical Technology CO., LTD., China), fursultiamine (Toronto Research Chemicals, Canada), or benfotiamine (Sigma-Aldrich, St. Louis, MO, USA), which are thiamine (vitamin B1) based compounds, were tested. For this, cortisol reduction effects in adrenal tumors that excessively secret cortisol were measured.

NCI-H295R (ATCC #CRL-2128) cells, a human adrenocortical carcinoma cell line, were dispensed into 24-well plates at $2.5\times10^5$ cells/well. Then, the cells were incubated in DMEM/F12 growth media containing 2.5% Nu-serum, 1% ITS (insulin, transferrin, and selenium), bovine serum albumin (BSA), linoleic acid, and penicillin/streptomycin for 48 hours.

Thereafter, the media were exchanged with serum-free media, and then the NCI-H295R cells were pretreated with allithiamine, fursultiamine, or benfotiamine at concentrations of 20 μM, 50 μM, and 100 μM for 12 hours. The cells were treated with 8-bromoadenosine 3',5'-cyclic monophosphate (8-Br-cAMP) at a concentration of 0.5 mM to increase cortisol synthesis, and again treated with allithiamine, fursultiamine, or benfotiamine at 20 μM, 50 μM, and 100 μM, followed by reaction for 24 hours. After the reaction, cell cultures were collected, and the amount of cortisol produced in the cells was measured using an enzyme-linked immunosorbent assay (ELISA) kit (Enzo Life Sciences, Inc., NY, USA).

It was verified that all of allithiamine, fursultiamine, and benfotiamine significantly inhibited the cortisol production, increased by the stimulation of 0.5 mM 8-Br-cAMP, in a dose-dependent manner.

Figure 1A:
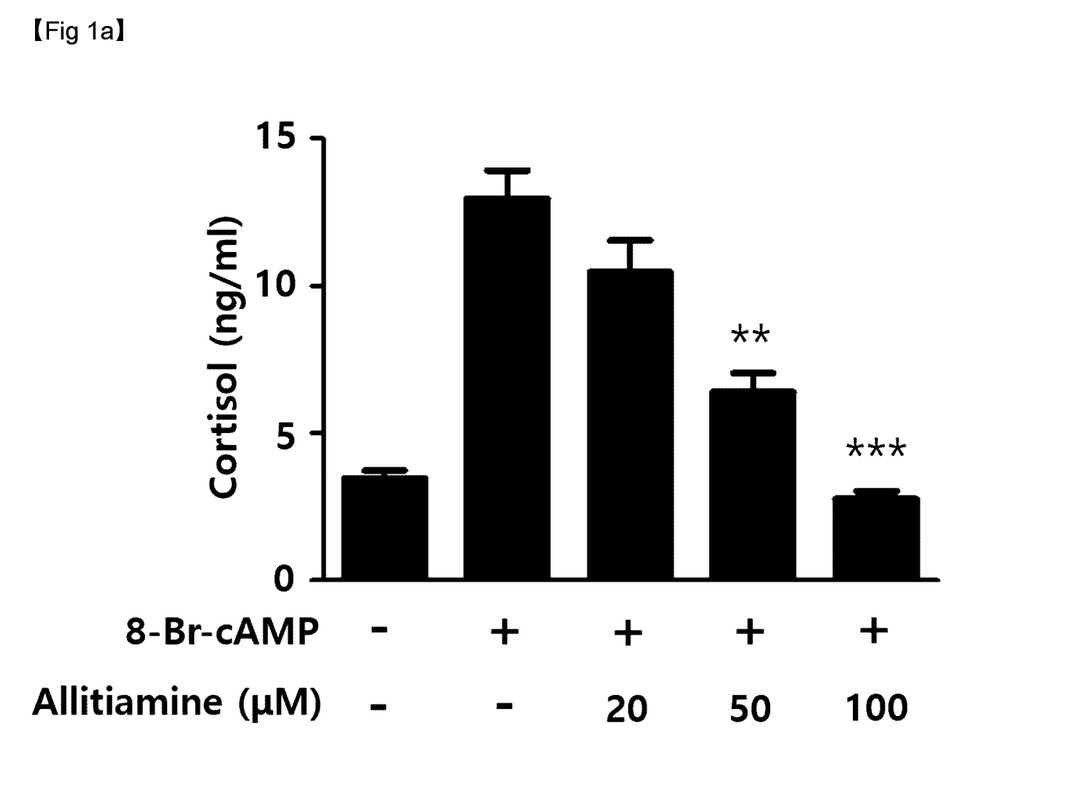
FIG. 1A is a graph depicting the test results of cortisol synthesis inhibitory ability after the treatment of the human adrenocortical carcinoma cell line NCI-H295R with allithiamine.
Figure 1B:
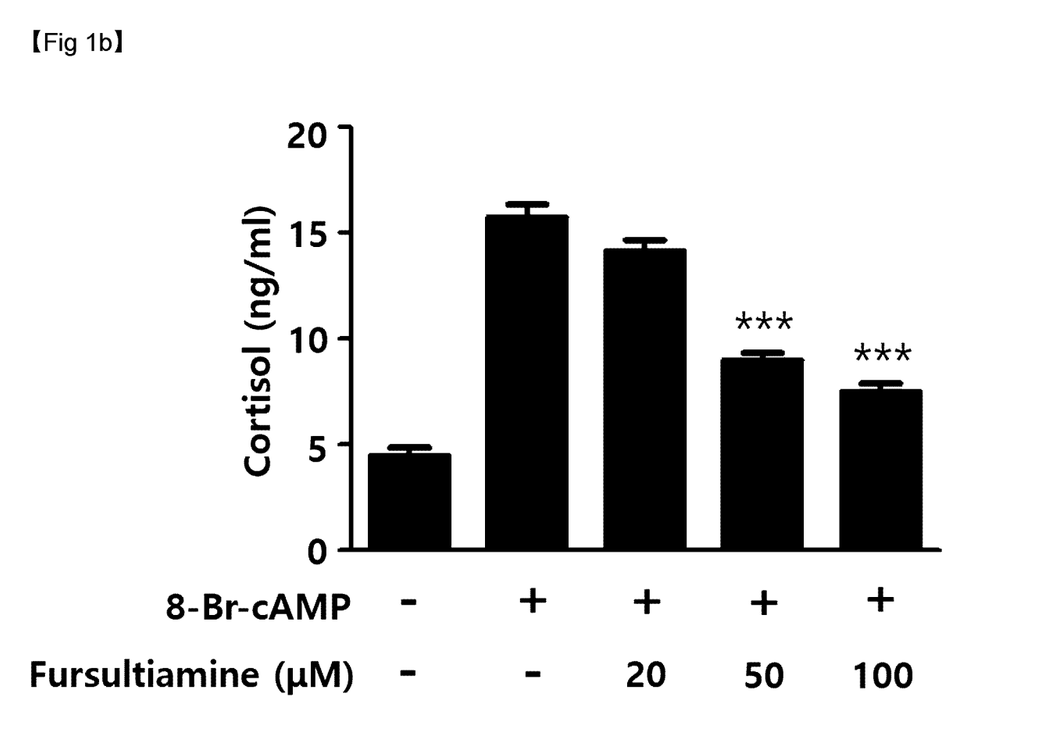
FIG. 1B is a graph depicting the test results of cortisol synthesis inhibitory ability after the treatment of the human adrenocortical carcinoma cell line NCI-H295R with fursultiamine.
Figure 1C:
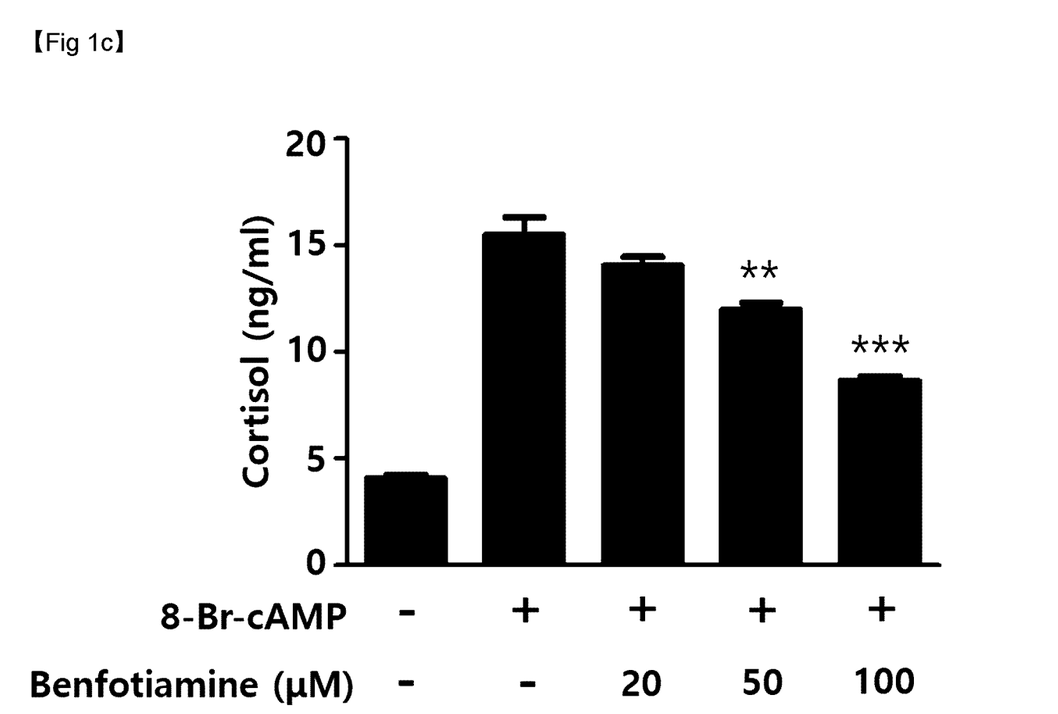
FIG. 1C is a graph depicting the test results of cortisol synthesis inhibitory ability after the treatment of the human adrenocortical carcinoma cell line NCI-H295R with benfotiamine.

Compared with the allithiamine non-treatment group (with 8-Br-cAMP treatment), the allithiamine treatment groups showed a reduction in cortisol production of 50.7% at 50 μM and 78.7% at 100 μM (see Table 1 and FIG. 1A). The fursultiamine treatment groups showed a reduction in cortisol production of 43% at 50 μM and 52.4% at 100 μM (see Table 2 and FIG. 1B). The benfotiamine treatment groups showed a reduction in cortisol production of 22.6% at 50 μM and 44.3% at 100 μM (see Table 3 and FIG. 1C) (p<0.01, *p<0.001 vs. 8-Br-cAMP treatment group).

TABLE 1

Cortisol production inhibitory effect of allithiamine

| 8-Br-cAMP (mM) | 0 | 0.5 | 0.5 | 0.5 | 0.5 |
|---|---|---|---|---|---|
| Allithiamine (μM) | 0 | 0 | 20 | 50 | 100 |
| Cortisol production concentration (ng/mL) | 3.5 | 13.0 | 10.5 | 6.4 | 2.8 |

TABLE 2

Cortisol production inhibitory effect of fursultiamine

| 8-Br-cAMP (mM) | 0 | 0.5 | 0.5 | 0.5 | 0.5 |
|---|---|---|---|---|---|
| Fursultiamine (μM) | 0 | 0 | 20 | 50 | 100 |
| Cortisol production concentration (ng/mL) | 4.5 | 15.7 | 14.1 | 9.0 | 7.5 |

TABLE 3

Cortisol production inhibitory effect of fursultiamine

| 8-Br-cAMP (mM) | 0 | 0.5 | 0.5 | 0.5 | 0.5 |
|---|---|---|---|---|---|
| Benfotiamine (μM) | 0 | 0 | 20 | 50 | 100 |
| Cortisol production concentration (ng/mL) | 4.1 | 15.5 | 14.0 | 12.0 | 8.6 |

Example 2: Verification of Cortisol Reduction Effects by Thiamine Derivatives In Vivo 2-1. Tests Using Cushing's Syndrome Animal Models To investigate high-cortisol inhibitory effects, C57BL/6J normal mice (WT-con) aged 8 to 9 weeks and corticotropin-releasing hormone (CRH)-overexpressed mice, which are Cushing's syndrome animal models, were used. One group of CRH-overexpressed mice were orally administered with 60 mg/kg fursultiamine once a day for 9 weeks (CRH tg-Fur 60 mpk).

During this period, the body weight change was monitored by measuring body weights once a week. To check the concentration of corticosterone (in cases of rodents), blood was collected from the tail vein and serum was isolated. The concentration of corticosterone was measured from the isolated serum by using an enzyme-linked immunosorbent assay (ELISA) kit (Enzo Life Sciences, Inc., NY, USA). The fat mass was measured 6 weeks after administration of the drug by using a body composition analyzer (MiniSpec LF 50, Bruker Optics, Germany), and the fat distribution was again monitored with micro CT images 8 weeks after administration.

Figure 2A:
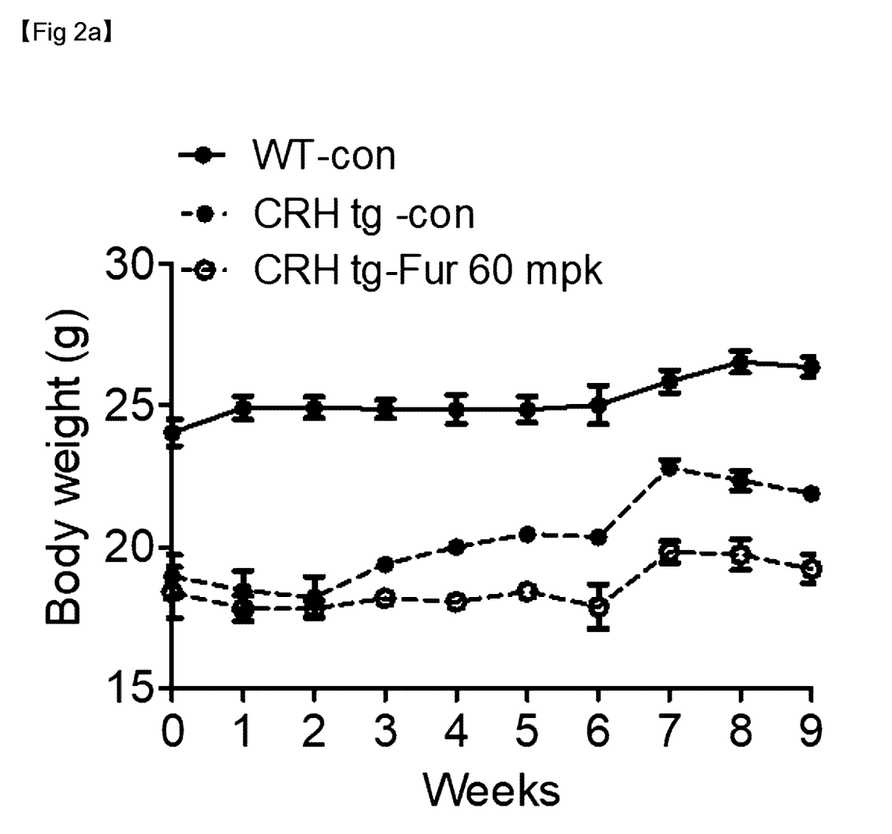
FIG. 2A is a graph depicting the body weight checking results to investigate the cortisol-induced obesity alleviating effect of fursultiamine in Cushing's syndrome animal models.

As can be verified in FIG. 2A and Table 4, the CRH-overexpressed mice showed a greater increase in body weight compared with the normal mice, whereas the CRH-overexpressed mice administered with fursultiamine showed a smaller increase in body weight compared with the control (CRH-overexpressed mice).

TABLE 4

| Weeks | Normal mice | CRH-overexpressed mice | CRH-overexpressed mice administered with fursultiamine |
|---|---|---|---|
| 0 | 24.0 | 19.0 | 18.4 |
| 1 | 24.9 | 18.5 | 17.8 |
| 2 | 24.9 | 18.2 | 17.8 |
| 3 | 24.9 | 19.4 | 18.2 |
| 4 | 24.9 | 20.0 | 18.1 |
| 5 | 24.9 | 20.5 | 18.4 |
| 6 | 25.0 | 20.4 | 17.9 |
| 7 | 25.8 | 22.8 | 19.8 |
| 8 | 26.5 | 22.4 | 19.7 |
| 9 | 26.4 | 21.9 | 19.2 |

Figure 2B:
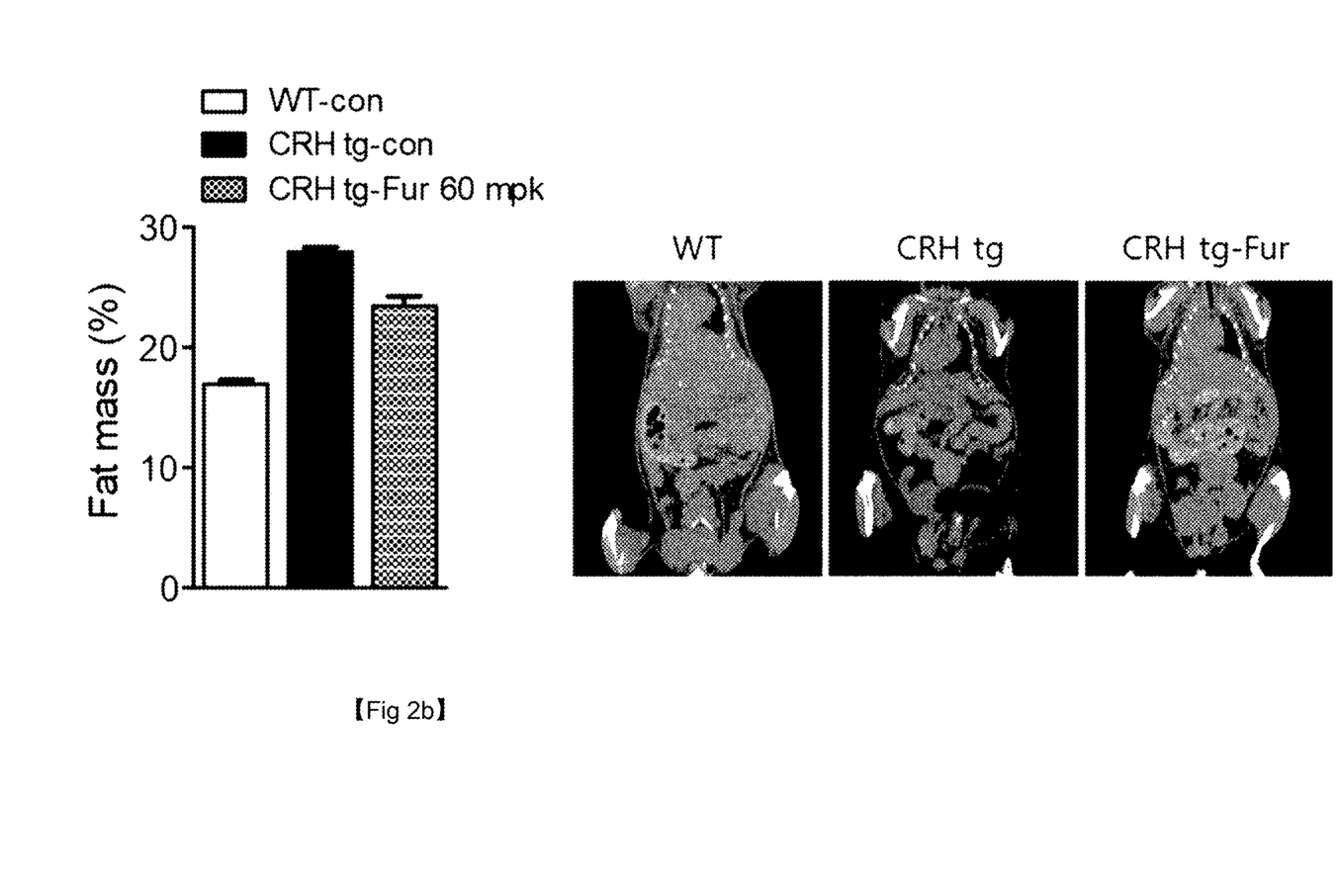
FIG. 2B shows images and a graph, which depict the fat mass checking results, to investigate the cortisol-induced obesity alleviating effect of fursultiamine in Cushing's syndrome animal models.

As can also be verified in FIG. 2B and Table 5, the fat mass of the CRH-overexpressed mice was greater compared with the normal mice, whereas the fat mass of the CRH-overexpressed mice administered with fursultiamine was smaller compared with the control.

TABLE 5

| | Normal mice | CRH-overexpressed mice | CRH-overexpressed mice administered with fursultiamine |
|---|---|---|---|
| Body weight (%) | 16.9 | 28.0 | 23.4 |

Figure 3:
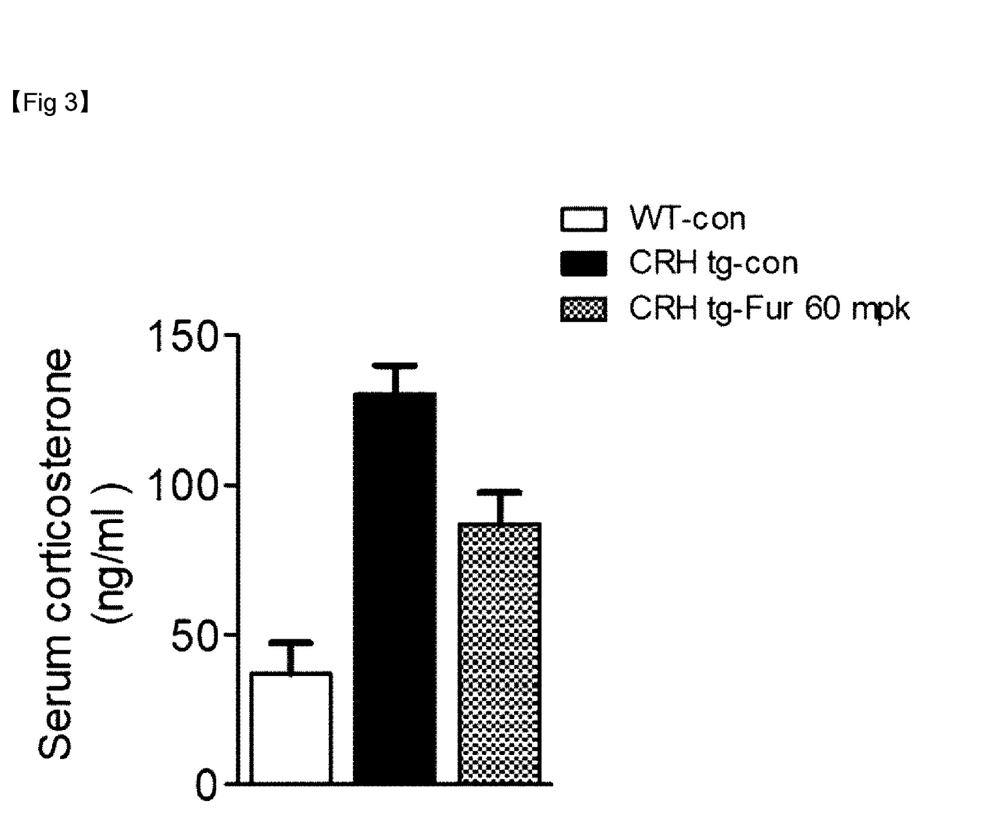
FIG. 3 shows a graph depicting the results of verifying cortisol inhibitory effects of fursultiamine in Cushing's syndrome animal models.

As can be verified in FIG. 3 and Table 6, the corticosterone synthesis concentration of the CRH-overexpressed mice was greater compared with the normal mice, whereas the corticosterone synthesis concentration of the CRH-overexpressed mice administered with fursultiamine was smaller compared with the normal group.

TABLE 6

| | Normal mice | CRH-overexpressed mice | CRH-overexpressed mice administered with fursultiamine |
|---|---|---|---|
| Corticosterone (ng/mL) | 37.0 | 130.5 | 87.1 |

Stress-Induced Test

For the restraint stress test, 8-week-old male mice were used, and were orally administered with fursultiamine once 24 hours before and once 2 hours before stress induction. For induction of stress, the mice were individually placed head-first into well-ventilated 50 mL polypropylene tubes, which were then tied with a cap of the 50 mL tube, and the mice were confined for 2 hours. Before stress induction, 1 hour and 2 hours after induction, and at 1 hour of recovery, blood was collected from the tail vein and serum was isolated, and then the concentration of corticosterone was measured using ELISA kit.

Figure 4:
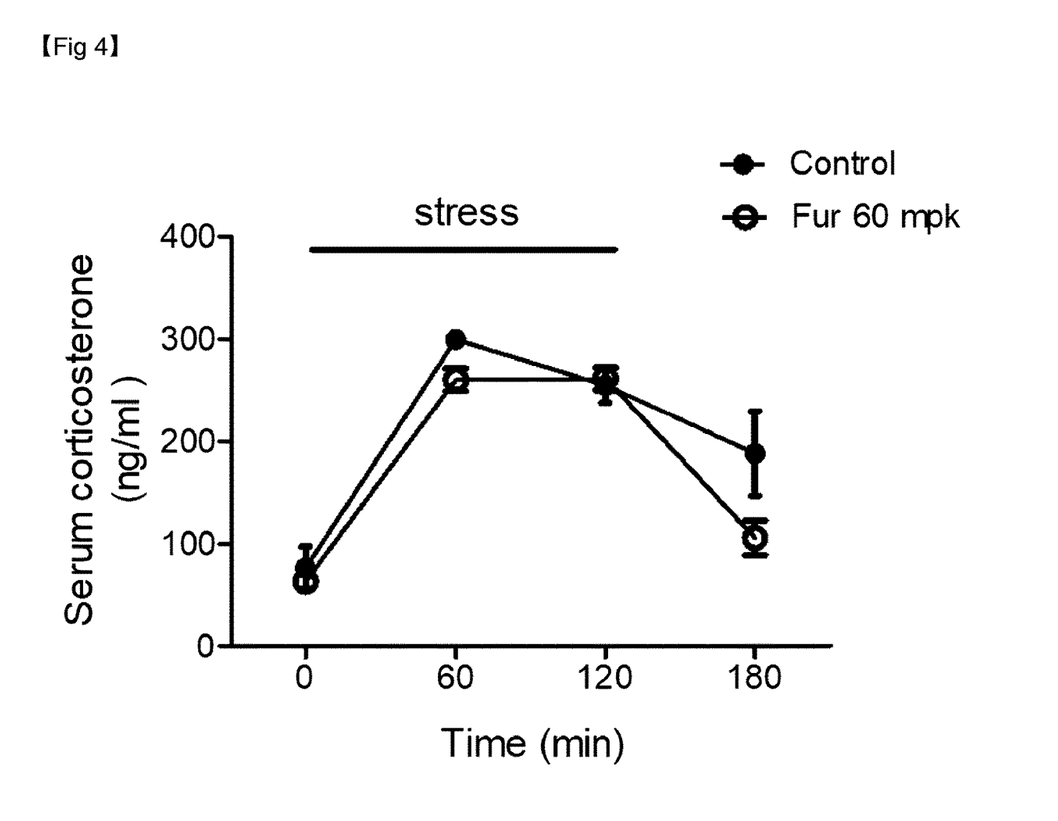
FIG. 4 shows a graph depicting the results of verifying cortisol synthesis inhibitory ability of fursultiamine in the stress-induced test.

As can be verified in FIG. 4 and Table 7, the corticosterone levels increased after stress induction, and the rate of increase in corticosterone level decreased in the fursultiamine administration group.

TABLE 7

| Time (min) | Control | Fursultiamine administration group |
|---|---|---|
| 0 | 76.6 | 63.6 |
| 60 | 300.0 | 260.4 |
| 120 | 255.1 | 261.4 |
| 180 | 188.3 | 105.8 |

INDUSTRIAL APPLICABILITY

The present disclosure relates to a composition containing a thiamine derivative for prevention or treatment of hypercortisolism and, more specifically, to a composition for prevention or treatment of hypercortisolism, the composition containing a thiamine derivative, a salt thereof, or a mixture composition thereof, the thiamine derivative being allithiamine, fursultiamine, or benfotiamine.

The invention claimed is:

1. A method for treating hypercortisolism in a subject, the method comprising the steps of:
   identifying a subject in need of treatment for hypercortisolism; and
   administering to the subject a pharmaceutical composition consisting of (i) fursultiamine or a pharmaceutically acceptable salt thereof, and (ii) optionally a pharmaceutically acceptable carrier,
   wherein the fursultiamine directly inhibits cortisol synthesis in adrenocortical cells, thereby treating hypercortisolism in the subject.

2. The method of claim 1, wherein the hypercortisolism is selected from the group consisting of Cushing's syndrome, Cushing's disease, and ectopic adrenocorticotropic hormone syndrome.

3. A method for treating cortisol-induced hypertension, cortisol-induced diabetes, cortisol-induced obesity or cortisol-induced depression in a subject, the method comprising the steps of:
   identifying a subject in need of treatment for cortisol-induced hypertension, cortisol-induced diabetes, cortisol-induced obesity or cortisol-induced depression; and
   administering to the subject a pharmaceutical composition consisting of (i) fursultiamine or a pharmaceutically acceptable salt thereof, and (ii) optionally a pharmaceutically acceptable carrier,
   wherein the fursultiamine directly inhibits cortisol synthesis in adrenocortical cells, thereby treating cortisol-induced hypertension, cortisol-induced diabetes, cortisol-induced obesity, or cortisol-induced depression in the subject.

* * * * *